United States Patent [19]
Wei et al.

[11] 3,962,228
[45] June 8, 1976

[54] 3-BENZOYLPROPIONAMIDO CEPHALOSPORANIC DERIVATIVES

[75] Inventors: Peter H. L. Wei, Springfield; Ronald J. McCaully, Malvern, both of Pa.

[73] Assignee: American Home Products Corporation, New York, N.Y.

[22] Filed: Mar. 18, 1974

[21] Appl. No.: 452,087

[52] U.S. Cl. .................. 260/243 C; 260/239.1; 424/246; 424/271
[51] Int. Cl.² .............. C07D 499/44; C07D 501/20
[58] Field of Search ................. 260/243 C

[56] References Cited
UNITED STATES PATENTS

| | | | |
|---|---|---|---|
| 3,855,213 | 12/1974 | Dunn et al. | 260/243 C |
| 3,867,380 | 2/1975 | Dunn et al. | 260/243 C |

Primary Examiner—Nicholas S. Rizzo
Attorney, Agent, or Firm—Richard K. Jackson

[57] ABSTRACT

The antibacterial agents of this invention present the following structural formula:

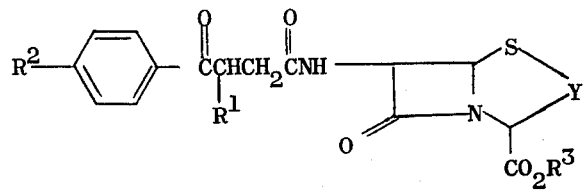

in which
$R^1$ is —OH, alkoxycarbonyloxy of 2 to 6 carbon atoms, arylsulfonyl of 6 to 10 carbon atoms or thiocyanato;
$R^2$ is —H, halo or phenyl;
$R^3$ is —H, an alkali metal or —NH₄; and
Y is

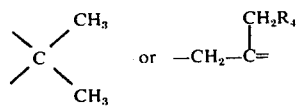

wherein
$R^4$ is —H, alkanoyloxy of 2 to 6 carbon atoms,

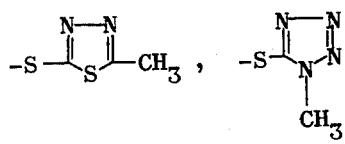

or
when taken with the 3-carboxy group,

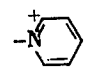

9 Claims, No Drawings

3-BENZOYLPROPIONAMIDO CEPHALOSPORANIC DERIVATIVES

DESCRIPTION OF THE INVENTION

In accordance with this invention there is provided antibacterial agents of the formula:

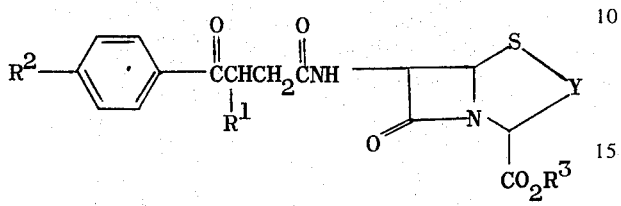

in which
$R^1$ is —OH, alkoxycarbonyloxy of 2 to 6 carbon atoms, arylsulfonyl of 6 to 10 carbon atoms or thiocyanato;
$R^2$ is —H, halo or phenyl;
$R^3$ is —H, an alkali metal or —NH$_4$; and
Y is

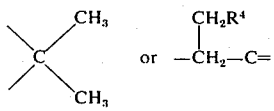

wherein
$R^4$ is —H, alkanoyloxy of 2 to 6 carbon atoms,

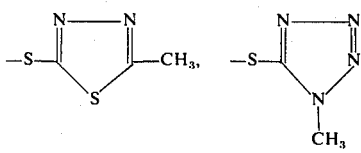

or when taken with the 3-carboxy group

The compounds of this invention are prepared by coupling techniques well known to the chemical arts. Thus, dehydrative coupling or mixed anhydride coupling as applied in the area of peptide synthesis are especially useful methods for the coupling reactions involved in the formation of the amides of 7-aminocephalosporanic acid derivatives and 6-amino penicillanic acid derivatives. In addition, the carboxylic acid initial reactants may, if desired, be converted to the corresponding acid halide by conventional means for use as the desired acylating agent.

The 3-disubstituted propionic acid reactants presenting the structural formula:

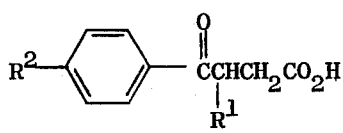

in which the groups $R^1$ and $R^2$ are defined above, are either known compounds (U.S. 3,714,218 and U.S. 3,749,750) or are prepared by techniques known to the chemist. For example, 3-(p-chlorobenzoyl)-3-hydroxypropionic acid is prepared by reacting 3-bromo-3-(p-chlorobenzoyl)propionic acid with aqueous 10 percent sodium carbonate. The same displacement reaction yields 3-(4-biphenylylcarbonyl)-3-hydroxypropionic acid from the 3-bromoprecursor.

The preferred group of compounds, from the standpoint of availability of the reactants, ease of reaction and production economics, are those of the formula:

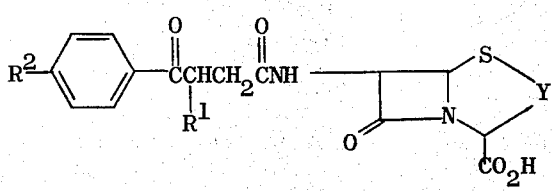

in which
$R^1$ is —OH, iso-butoxycarbonyloxy, tolylsulfonyl or thiocyanato;
$R^2$ is —Cl or phenyl; and
Y is

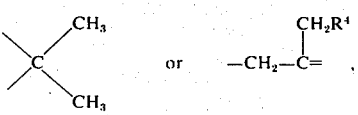

wherein
$R^4$ is —H or acetoxy.

The compounds of this invention have been found to be active antibacterials effective against gram-positive and gram-negative test organisms as well as penicillin resistant staphlococcus, by using the well known and scientifically accepted agar serial dilution testing technique. Thus, the compounds of this invention are useful in the fields of comparative pharmacology and in microbiology and may be used for the treatment of bacterial infections amenable to treatment with penicillin and infestations antibiotics. occurred.

The following examples illustrate the preparation of representative penicillin and cephalosporin derivatives. The activity of each product of the examples is presented for those specific bacterial strains against which the compound exemplified was active at or below 250 micrograms per milliliter. The representative nature of the bacterial strains employed to demonstrate antibacterial activity are indicative of the broader applicability of the compounds of this invention in the control of bacterial infections other than those specifically referred to in each of the following examples. The bacterium are named followed by the specific strain and the concentration in micrograms per milliliter at which 100 percent inhibition occured. The abbreviations for each bacterium are:

| | |
|---|---|
| BA SU | *Bacillus subtilis* |
| BO BR | *Bordetella bronchiseptica* |
| ES CO | *Escherichia coli* |
| HE SP | *Herellea species* |
| KL PN | *Klebsiella penumoniae* |
| NE CA | *Neisseria catarrhalis* |
| PR VU | *Proteus vulgaris* |
| SA PA | *Salmonella paratyphi* |

-continued

ST AU  Staphylococcus aureus

EXAMPLE I

7-[3-(p-Chlorobenzoyl)-3-hydroxypropionamido]-cephalosporanic acid isobutyl carbonate.

To a tetrahydrofuran solution of 1.14 grams (5 millimole) of 3-(p-chlorobenzoyl)-3-hydroxypropionic acid in a salt-ice bath was added triethyl amine (10 millimole) followed by isobutyl chloroformate. After the solution was stirred for 15 minutes a cold solution of 1.36 grams (5 millimole) of 7-aminocephalosporanic acid and 0.50 gram triethylamine in a mixture of 20 milliliter tetrahydrofuran and 10 milliliters $H_2O$ was slowly added. Some insoluble material was filtered off. The solvent was removed at reduced pressure around 30°C. The residue was dissolved in 50 milliliters $H_2O$ and a small amount of insoluble material was filtered. Acidification of the aqueous solution 6N hydrochloric acid caused a solid to precipitate which was collected and washed with water. An ethyl acetate solution of the crude solid was dried over anhydrous $MgSO_4$. After the solvent was removed the solid residue was treated with pentane and collected to give 2.0 grams polymorphous product.

Elemental Analysis for $C_{25}H_{27}ClN_2O_{10}S$: Calc'd: C, 51.50; H, 4.67; N, 4.81. Found: C, 52.10; H, 4.70; N, 4.63.

| BA SU | 6633 | 1.95 |
| --- | --- | --- |
| HE SP | 9955 | 250 |
| KL PN | 10031 | 125 |
| NE CA | 8193 | 250 |
| PR VU | 6896 | 125 |
| SA PA | 11737 | 250 |
| ST AU | 6538P | 1.95 |
| ST AU | SMITH | 1.95 |
| ST AU | CHP | 7.81 |
| ST AU | 53–180 | 3.90 |

EXAMPLE II

6-[3-(p-Chlorobenzoyl)-3-(p-tolylsulfonyl)propionamido]penicillanic acid.

The titled compound was obtained by following the procedure of Example 1, in which equimolar quantities of 6-amino penicillanic acid, and 3-(p-chlorobenzoylyl)-3-(p-tolylsulfonyl)propionic acid were utilized.

Elemental Analysis for $C_{25}H_{25}ClN_2O_7S_2 \cdot 1/2H_2O$: Calc'd: C, 52.30; H, 4.57; N, 4.88. Found: C, 52.36; H, 4.52; N, 4.35.

| BA SU | 6633 | 3.90 |
| --- | --- | --- |
| HE SP | 9955 | 125 |
| KL PN | 10031 | 250 |
| NE CA | 8193 | 7.81 |
| PR VU | 6896 | 250 |
| ST AU | 6538P | .976 |
| ST AU | SMITH | .976 |
| ST AU | CHP | 31.3 |
| ST AU | 53–180 | 125 |

EXAMPLE III

7-[3-(p-chlorobenzoyl)-3-(p-tolylsulfonyl)propionamino]cephalosporanic acid.

The titled compound was obtained by following the procedure of Example I in which an equimolar quantity of 3-(p-chlorobenzoyl)-3-(p-tolylsulfonyl)propionic acid was employed.

Elemental Analysis for $C_{27}H_{25}ClN_2O_9S_2$: Calc'd: C, 52.50; H, 4.06; N, 4.51. Found: C, 52.11; H, 4.05; N, 3.90.

| BA SU | 6633 | .976 |
| --- | --- | --- |
| KL PN | 10031 | 62.5 |
| NE CA | 8193 | 250 |
| PR VU | 6896 | 125 |
| SA PA | 11737 | 125 |
| ST AU | 6538P | 1.95 |
| ST AU | SMITH | 1.95 |
| ST AU | CHP | 3.90 |
| ST AU | 53–180 | 3.90 |

EXAMPLE IV

7-[3-(p-Chlorobenzoyl)-3-)p-tolylsulfonyl)propionamido]-3-methyl-8-oxo-5-thia-1-azabicyclo[4.2.0]oct-2-ene-2-carboxylic acid.

The titled compound was obtained by following the procedure of Example I in which equimolar quantities of 3-(p-chlorobenzoyl)-3-(p-tolylsulfonyl)propionic acid and 7-aminodesacetoxycephalosporanic acid were utilized.

Elemental Analysis for $C_{25}H_{23}ClN_2O_7S_2$: Calc'd: C, 53.33; H, 4.12; N, 4.97. Found: C, 53.06; H, 4.16; N, 4.50.

| BA SU | 6633 | 15.6 |
| --- | --- | --- |
| ST AU | 6538P | 15.6 |
| ST AU | SMITH | 15.6 |
| ST AU | CHP | 62.5 |
| ST AU | 53–180 | 31.3 |

EXAMPLE V

7-[3-(p-Chlorobenzoyl)-3-hydroxypropionamido]-3-methyl-8-oxo-5-thia-1-azabicyclo[4.2.0]oct-2-ene-2-carboxylic acid.

The title compound was obtained by following the procedure of Example I, in which an equimolar quantity of 7-aminodesacetoxycephalosporanic acid was utilized.

Elemental Analysis for $C_{18}H_{17}ClN_2O_6S$: Calc'd: C, 50.86; H, 4.03; N, 6.60. Found: C, 51.93; H, 4.12; N, 6.34.

| BA SU | 6633 | 31.3 |
| --- | --- | --- |
| HE SP | 9955 | 125 |
| PR VU | 4617 | 125 |
| ST AU | 6538P | 15.6 |
| ST AU | SMITH | 15.6 |
| ST AU | CHP | 31.3 |
| ST AU | 53–180 | 31.3 |

EXAMPLE VI

6-[3-(4-Biphenylylcarbonyl)-3-hydroxypropionamido]penicillanic acid.

The title compound was prepared by following the procedure of Example I in which equimolar quantities of 3-(4-biphenylylcarbonyl)-3-hydroxypropionic acid and 6-aminopenicillanic acid were utilized.

Elemental Analysis for $C_{24}H_{24}N_2O_6S$: Calc'd: C, 61.53; H, 5.16; N, 5.98. Found: C, 61.74; H, 5.40; N, 6.22.

| BA SU | 6633 | 1.95 |
|---|---|---|
| HE SP | 9955 | 62.5 |
| NE CA | 8193 | 7.81 |
| ST AU | 6538P | .244 |
| ST AU | SMITH | .244 |
| ST AU | CHP | 15.6 |
| ST AU | 53–180 | 31.3 |

EXAMPLE VII

6-[3-(p-Chlorobenzoyl)-3-thiocyanatopropionamido]penicillanic acid potassium salt.

3-(p-Chlorobenzoyl)-3-thiocyanatopropionic acid (1.40 grams, 5 millimole) was dissolved in 5 milliliter dimethylformamide. Carbonyl diimidazole (0.82 gram, 5 millimole) was added in one portion. The mixture was stirred under nitrogen for ½ hour and evacuated for ½ hour. To the above solution, chilled in an ice bath, was added a cold solution of 1.08 grams (5 millimole) 6-aminopenicillanic acid and 1.00 gram (10 millimole) of triethylamine in methylene chloride. The reaction mixture was stirred, in the ice bath for 2 hours, filtered, and concentrated in vacuo at 30°C. To the residue dissolved in methylene chloride was added a solution of 1 milliliter of a 2 Molar potassium salt of 2-ethyl hexanoate in propanol. Addition of anhydrous ether caused precipitation of the potassium salt, which was collected, washed with ether, and dried.

Elemental Analysis for $C_{19}H_{17}ClN_3O_5S_2K.H_2O$: Calc'd: C, 43.55; H, 3.66; N, 8.02. Found: C, 43.85; H, 3.48; N, 8.63.

| BA SU | 6633 | 62.5 |
|---|---|---|
| HE SP | 9955 | 250 |
| NE CA | 8193 | 250 |
| ST AU | 6538P | 15.6 |
| ST AU | SMITH | 15.6 |
| ST AU | CHP | 125 |
| ST AU | 53–180 | 125 |

EXAMPLE VIII

7-[3-(p-Chlorobenzoyl)-3-thiocyanatopropionamido]cephalosporanic acid, potassium salt.

The title compound was prepared by following the procedure of Example 7 in which 7-aminocephalosporanic acid was utilized.

Elemental Analysis for $C_{21}H_{17}ClN_3O_7S_2K.1/4(C_2H_5)_2O.1½H_2O$: Calc'd: C, 42.94; H, 3.69; N, 6.99. Found: C, 42.11; H, 3.02; N, 6.38.

| BA SU | 6633 | 1.95 |
|---|---|---|
| BO BR | 4617 | 250 |
| ES CO | 9637 | 250 |
| KL PN | 10031 | 62.5 |
| NE CA | 8193 | 250 |
| PR VU | 6896 | 250 |
| SA PA | 11737 | 125 |
| ST AU | 6538P | 3.90 |
| ST AU | SMITH | 3.90 |
| ST AU | CHP | 15.6 |
| ST AU | 53–180 | 15.6 |

EXAMPLE IX

7-[3-(4-Biphenylylcarbonyl)-3-hydroxypropionamido]cephalosporanic acid.

The title compound was prepared by following the procedure of Example 1, in which 3-(4-biphenylylcarbonyl)-3-hydroxypropionic acid was utilized.

Elemental Analysis for $C_{26}H_{24}N_2O_8S$: Calc'd: C, 59.55; H, 4.61; N, 5.34. Found: C, 59.64; H, 4.53; N, 5.26.

| BA SU | 6633 | 3.90 |
|---|---|---|
| HE SP | 9955 | 250 |
| KL PN | 10031 | 250 |
| NE CA | 8193 | 250 |
| SA PA | 11737 | 250 |
| ST AU | 6538P | 1.95 |
| ST AU | SMITH | 1.95 |
| ST AU | CHP | 3.90 |
| ST AU | 53–180 | 3.90 |

EXAMPLE X

7-[3-(4-Biphenylylcarbonyl)-3-thiocyanatopropionamido]cephalosporanic acid, potassium salt.

The title compound was prepared by following the procedure of Example 7, in which 3-(4-biphenylcarbonyl)-3-thiocyanatopropionic acid and 7-aminocephalosporanic acid were utilized.

Elemental Analysis for $C_{27}H_{22}N_3O_7S_2K$: Calc'd: C, 53.71; H, 3.68; H, 6.96. Found: C, 53.53; H, 3.53; N, 6.74.

| BA SU | 6633 | 3.90 |
|---|---|---|
| ES CO | 9637 | 250 |
| KL PN | 10031 | 62.5 |
| NE CA | 8193 | 250 |
| PR VU | 6896 | 125 |
| SA PA | 11737 | 125 |
| ST AU | 6538P | 3.90 |
| ST AU | SMITH | 3.90 |
| ST AU | CHP | 31.3 |
| ST AU | 53–180 | 15.6 |

What is claimed is:

1. A compound of the formula:

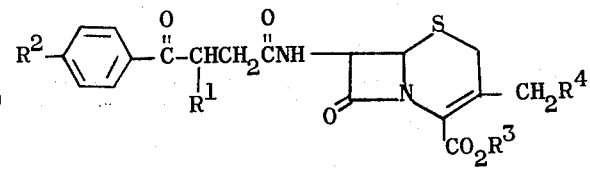

in which
R¹ is —OH, alkoxycarbonyloxy of 2 to 6 carbon atoms, arylsulfonyl of 6 to 10 carbon atoms or thiocyanato;
R² is —H, halo or phenyl;

$R^3$ is —H, an alkali metal or —$NH_4$, and
$R^4$ is —H, alkanoyloxy of 2 to 6 carbon atoms, or when taken with the 3-carboxy group,

 .

2. The compound of claim 1 which is 7-[3-(p-chlorobenzoyl)3-hydroxypropionamido]cephalosoporanic acid isobutyl carbonate.

3. The compound of claim 1 which is 7-[3-(p-chlorobenzoyl)3-(p-tolylsulfonyl)propionamido]cephalosporanic acid.

4. The compound of claim 1 which is 7-[3-(p-chlorobenzoyl)3-(p-tolylsulfonyl)-propionamido]-3-methyl-8-oxo-5-thia-1-azabicyclo[4.2.0]oct-2-ene-2-carboxylic acid.

5. The compound of claim 1 which is 7-[3-(p-chlorobenzoyl)3-hydroxypropionamido]-3-methyl-8-oxo-5-thia-1-azabicyclo[4.2.0]oct-2-ene-2-carboxylic acid.

6. The compound of claim 1 which is 7-[3-(p-chlorobenzoyl)3-thiocyanatopropionamido]cephalosporanic acid.

7. The compound of claim 1 which is 7-[3-(4-biphenylylcarbonyl)-3-hydroxypropionamido]cephalosporanic acid.

8. The compound of claim 1 which is 7-[3-(4-biphenylylcarbonyl)-3-thiocyanatopropionamido]-cephalosporanic acid.

9. A compound of claim 1 of the formula:

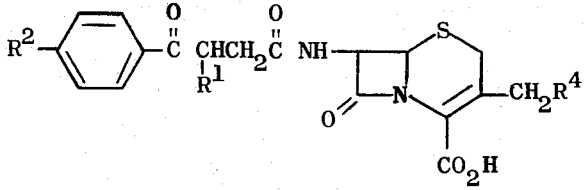

in which
$R^1$ is —OH, iso-butoxycarbonyloxy, tolylsulfonyl or thiocyanato;
$R^2$ is —Cl or phenyl; and
$R^4$ is —H or acetoxy;

* * * * *